(12) United States Patent
Busch et al.

(10) Patent No.: US 8,117,010 B2
(45) Date of Patent: Feb. 14, 2012

(54) SPECTRAL SIGNAL DETECTION SYSTEM

(75) Inventors: Darryl Busch, Eden Prairie, MN (US);
Kwong Wing Au, Bloomington, MN
(US); Michael John Flanagan, St.
Petersburg, FL (US); Saad J. Bedros,
West St. Paul, MN (US); **Mirela
Onorica Popa**, Cornelius, NC (US)

(73) Assignee: Honeywell International Inc.,
Morristown, NJ (US)

( * ) Notice: Subject to any disclaimer, the term of this patent is extended or adjusted under 35 U.S.C. 154(b) by 561 days.

(21) Appl. No.: 12/329,432

(22) Filed: Dec. 5, 2008

(65) Prior Publication Data

US 2010/0145659 A1    Jun. 10, 2010

(51) Int. Cl.
*G06F 15/00* (2006.01)
(52) U.S. Cl. ........ 702/190; 250/221; 250/235; 356/303; 356/308
(58) Field of Classification Search .................. 702/190; 250/221, 236; 356/303–308
See application file for complete search history.

(56) References Cited

U.S. PATENT DOCUMENTS

| | | | |
|---|---|---|---|
| 4,221,966 A | 9/1980 | Kerr et al. | |
| 4,678,332 A | 7/1987 | Rock et al. | |
| 6,862,535 B2 | 3/2005 | Binder | |
| 7,096,125 B2 | 8/2006 | Padmanabhan et al. | |
| 7,242,806 B2 | 7/2007 | Johnson et al. | |
| 2007/0093970 A1 | 4/2007 | Padmanabhan et al. | |

FOREIGN PATENT DOCUMENTS

WO    03054824    7/2003

*Primary Examiner* — Drew A Dunn
*Assistant Examiner* — Hien Vo
(74) *Attorney, Agent, or Firm* — Seager, Tufte & Wickhem, LLC

(57) ABSTRACT

A detection system which provides for continuous background estimation removal from a sequence of spectra. A panoramic field of regard may be partitioned into a large number of fields of view (FOVs). An FOV may have a chemical vapor cloud. The small FOV may maximize detection of the cloud. Such detection may require removing the spectral characteristics other than that of the target cloud. This may amount to removal of background spectra with an estimated background developed from one or more FOVs which may or may not be similar to the background of the FOV with the target cloud. A number of estimated background spectra of the other FOVs may be used individually to greatly increase the detection probability of the target chemical.

20 Claims, 15 Drawing Sheets

SPECTRAL SIGNAL DETECTION SYSTEM

The U.S. Government may have certain rights to the present invention.

BACKGROUND

The invention pertains to detection of spectra and particularly to detection of certain spectra among other spectra such as background and interferent.

SUMMARY

The invention is a detection system that provides for background removal from a field of view (FOV) of spectra. A panoramic field of regard may be partitioned into a large number of FOVs. An FOV may include spectra including that of a target substance. Such detection may require removing the spectra other than that of the target. This may amount to removal of the system artifacts and the background with an estimated background developed from spectra of one or more FOVs which may or may not be similar to the background of the FOV with the target. For examples, a number of estimated background spectra of the other FOVs may be used individually to greatly increase the detection probability of the target substance.

DESCRIPTION

Figure 1:
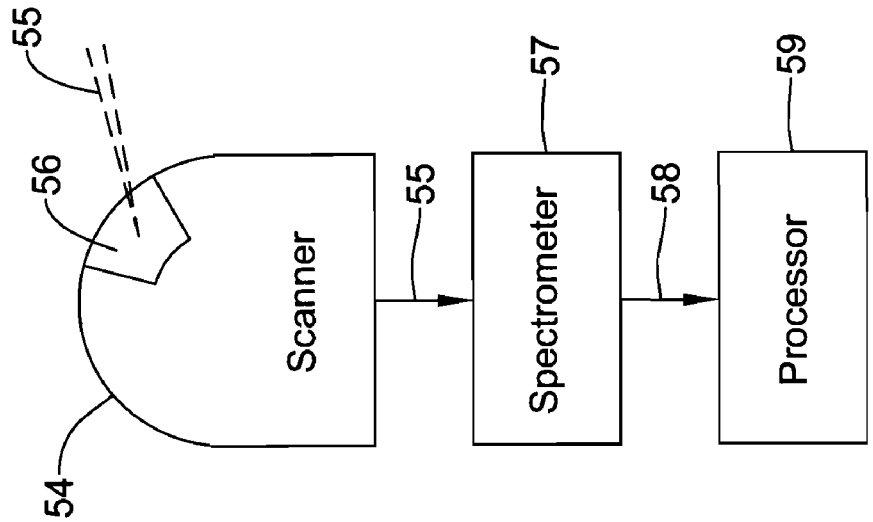
FIG. 1 is a diagram of an illustrative apparatus used for the present system.

The present invention relates to identification of small signals embedded in a large background signal. The system may be for extracting a target vapor cloud spectrum that is embedded in a background spectrum. The system may be a remote chemical detection system using a scanning spectrometer where an entire panoramic field of regard (FOR) can be partitioned into hundreds, thousands or more field of views (FOV's). The large number of FOV's is due a desire to have a large FOR, with negligible gaps between FOV's, and to use a small FOV so that it can be filled by a small, distant cloud and thus maximize the cloud signal. The objective of the system is to detect, if any, one or more target chemicals in each FOV. The radiance, thus the resulting spectrum, of each FOV may include those from the background, the atmosphere, other chemical clouds, and, if any, the target chemical cloud. A contribution of the spectral signal from the target chemical cloud may be a very small fraction of the total spectrum. Detection of the target chemical with high sensitivity may require removing spectral characteristics other than those of the target chemical cloud.

A signal from a spectrometer may need calibration to correct the signal's bias and gain, to sample at the correct frequency comb. Due to design constraints or inaccurate calibration, system artifacts may be introduced into the spectrum. These system artifacts often interfere and distort the spectral characteristics of the target chemical causing a poor detection performance.

The system artifacts, whose magnitude is based on the dynamics between the external and internal temperatures and system response, may vary from system to system and with time. Therefore, it appears difficult to model and remove artifacts solely from an input spectrum and the calibration information.

Background and constituents in the atmosphere, such as ozone and water, may introduce their own spectral signatures, which also interfere and distort a target chemical spectral signal. In order to achieve high detection sensitivity, these unwanted spectral characteristics should be removed.

Some systems may apply a background subtraction approach, which recursively estimates and stores a reference background for each FOV from the spectrum of the same FOV, to alleviate these issues. These systems, however, are limited to be stationery deployments with only a few FOV's as the whole FOR. The limitation arises because a small FOV is more sensitive to small distant clouds (the cloud fills the FOV), but more FOV's are required to fill the FOR. Hardware limitation and software management may prevent storing background references in a large FOR. In non-stationary applications, the platform is moving and each FOV is potentially unseen before, and so acquiring the reference background without the target chemical cloud might not be possible.

The system may estimate "n" background spectra from spectra of n most recently scanned nearby FOV's that are classified as not having the target chemical. The current input spectrum and n nearby spectra may be acquired as the scanner rapidly scans across the FOR and onto a cloud. The input spectrum may be subtracted from each of these n spectra. Also, each estimated background spectrum may be subtracted from the input spectrum. The resulting 2n difference spectra may be subjected to a "boosting" process, where the boosting factor is dependent on the amount of background and atmospheric clutter in the input spectrum and nearby spectrum. The boost may represent confidence in any peaks in the difference spectrum. If the input spectrum and nearby spectrum are relatively clutter-free, then the difference spectra may be amplified accordingly. If there is strong clutter, then the difference spectrum should be amplified less or attenuated. Each boosted difference spectrum may then be classified to have or not to have the target chemical. If any of the spectra positively represents the target chemical, then the input spectrum may be classified as having the target chemical.

Since the input and the estimated background radiances pass through the same system components, the resulting spectra may have the same system artifacts. The difference between the radiances does not necessarily have the system artifact characteristics.

Since the estimated background spectrum may be derived from a spectrum of most recent FOV's, which is adjacent to or close to the input FOV, the background and atmospheric constituents could be very similar. Again the difference between the input spectrum and the estimated background spectrum should remove most, if not all, the spectral characteristics from the background and atmosphere.

A feature of the system may include using n estimated background spectra individually. Treating each of these n background estimates individually should greatly increase the detection probability of the target chemical. If the background is changing rapidly, then the closest FOV's may provide the best difference spectrum. If the cloud edge is fuzzy, then a detectable difference spectrum may not necessarily be obtained until the current FOV is near the middle of the cloud and a suitably contrasting background is several (n) FOV's back.

The system does not necessarily use the spectrum from close-by FOV's for an estimation of background spectra, as many conventional approaches do. Rather the estimated background spectra may be derived from the close-by FOV's' spectra such that the estimated background spectra optimally match with the input spectra as indicated in the following equation, $$\text{Est. Background Spec} = C_1 * \text{Spec}_{fov} + C_2 + C_3 * X,$$

where $\text{Spec}_{fov}$ is the spectrum of a nearby FOV, and X is a linear line, effectively adjusting the slope of the background. $C_1$, $C_2$ and $C_3$ are constants that may be automatically computed to maximally match the background spectral region (regions outside of the target chemical peaks). Constraints may be applied to values of C avoiding over-correction.

Another feature of the system may include a boosting/de-boosting of the difference spectrum. The difference spectrum may be scaled by a factor which varies depending on the amount of clutter in the background spectra. The clutter from common atmospheric peaks may be calculated before the difference spectrum. This approach may amplify the target chemical signal when the situation permits, and attenuate the background signal when background clutter is detected and there is lower confidence that the residual peaks in the difference spectrum are real.

The system may provide a safe measure that prevents the usage of an estimated background that is drastically different from the input spectrum. When the total energy of a difference spectrum exceeds a certain threshold, the estimated background spectrum will not necessarily be used for detection. This feature may avoid leakage of false background characteristics into the input FOV. The remaining n−1 background estimates may still be used for background removal.

The system may be coded in software executables in GPC or DSP. A parameter file that stores the values of parameters may accompany the executable and be loaded into the GPC or DSP for the specific list of target chemicals.

The standoff chemical vapor detector may be fully automatic and provide real-time, on the move detection for contamination avoidance and reconnaissance operations on a wide variety of land, air, space and sea platforms. A passive, remote Fourier transform infrared (FTIR) spectroscopy may be used to sense chemical clouds at a distance using only thermal emission from the scene.

FIG. 1 shows an instance of an apparatus used for the present system. A scanner 54 may be used for directing the radiance 55 from the FOV's of the field of regard via a window 56. The radiance 55 may go through a set of optics and into a spectrometer 57. The optics may be in either the scanner 54 or the spectrometer 57, or both. The spectrometer may detect and/or measure wavelengths of radiance 55. The radiance 55, including amplitudes and/or wavelength information, may be converted to an electrical signal 58 representing radiance 55 and provided to a processor 59. Processor 59 may calculate, for example, a spectrum of a target with the background effectively removed, provide graphical representations of the spectra, possibly identify the target such as a chemical cloud, and so forth.

Figure 2:
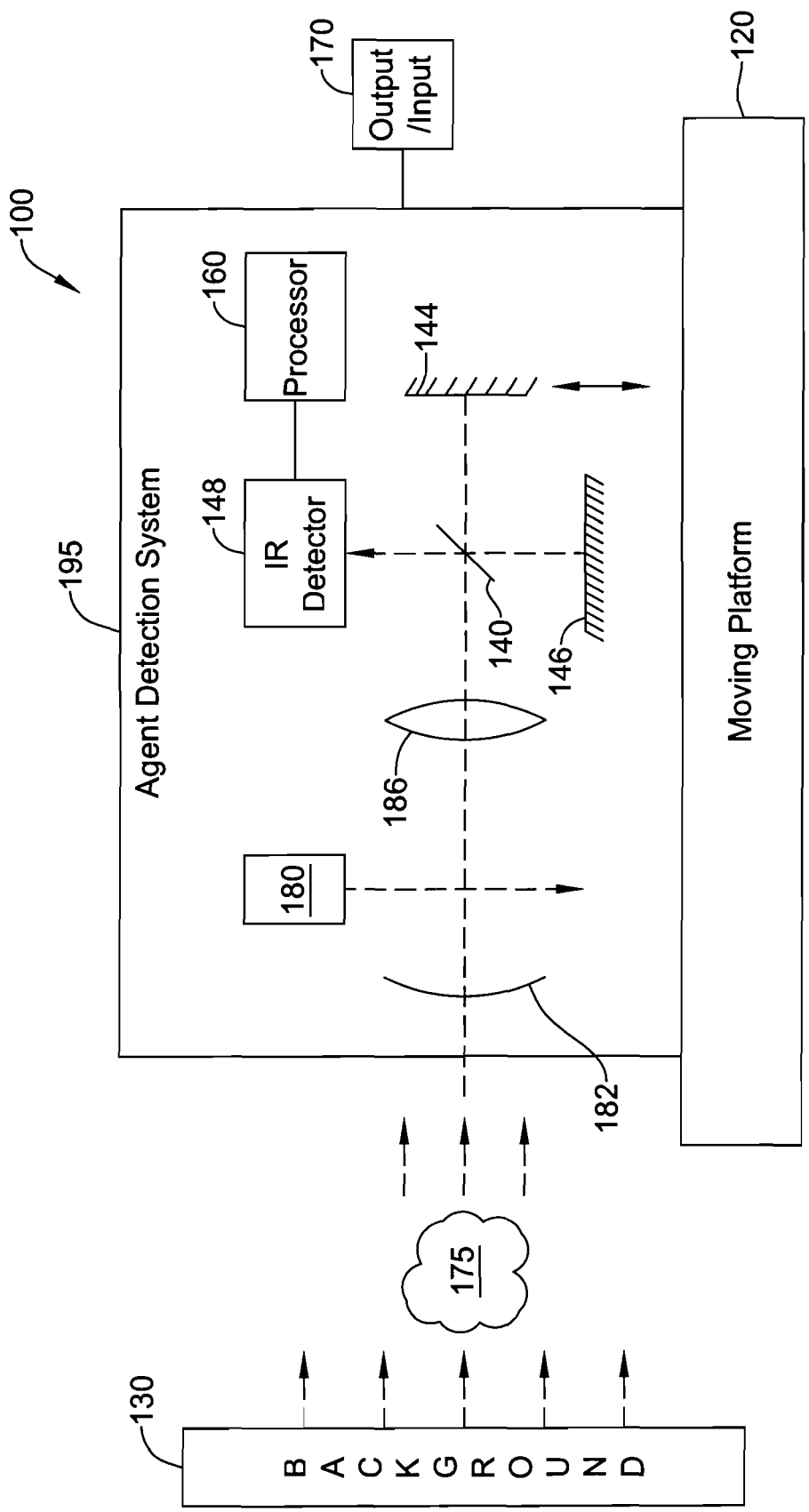
FIG. 2 is a block diagram of a passive mobile chemical agent detection system.

The chemical vapor detection system for use in detecting target chemical clouds in a mobile setting is shown generally at 100 in FIG. 2. The system may be housed in an enclosure 195 and mounted on a moving platform 120, such as a moving vehicle, whether ground, water, space or air based. The platform may also be stationary at a fixed site. The chemical vapor detection system 100 may be used to detect and differentiate target chemical vapors 175 by class and by type with a very low false alarm rate. To meet this objective, a large field of regard (FOR) may be interrogated within defined time constraints on many application platforms under numerous conditions. Examples of target chemicals to be detected may include classes of nerve, blister and blood chemical agents. Each class may have many agent species. Numerous conditions may include ideal and real battlespace environments, with or without common battlefield interferents, and views of various types of backgrounds 130. Applications may include sea, land, space or air operation while stationary or on a moving platform.

One type of chemical vapor detection system utilized may employ passive sensing of infrared (IR) emissions. The emissions, along with background emissions may be received through a lens or window 182 mounted in the enclosure 195, and focused by a lens system 186 onto a beam splitter element 140. Some of the IR may be transmitted by a first stationary mirror 144 mounted behind the beam splitter element 140. The rest of the IR may be reflected by element 140 onto a moving mirror 146. The reflected beams from the stationary mirror 144 and moving mirror 146 may combine to create an interference pattern, which is detected by an IR detector 148. An output of the IR detector may be sampled at high or medium resolutions in one of two modes to create an interferogram, which is processed at a processor 160 to provide an output 170 such as a decision regarding whether or not a chemical cloud exists.

Figure 3:
FIG. 3 is a high level block flow diagram of the chemical agent detection system of FIG. 2.

In a search mode as indicated at 210 in FIG. 3, a reduced resolution may be utilized at approximate a 16 wavenumber resolution. When potential agents are detected, the mode may be switched at 220 to a confirmation mode with sequential decision making at 230. At 240, the extent of the potential threat may be mapped to provide an indication of the size and location of the chemical cloud.

A background estimation (BE) approach may purify spectral data by removing background features and system artifacts. The approach may have preprocessing, feature extraction and classification. The approach may also have on-themove detection capability, current field of regard (FOR), and real-time results and reporting.

Figure 13:
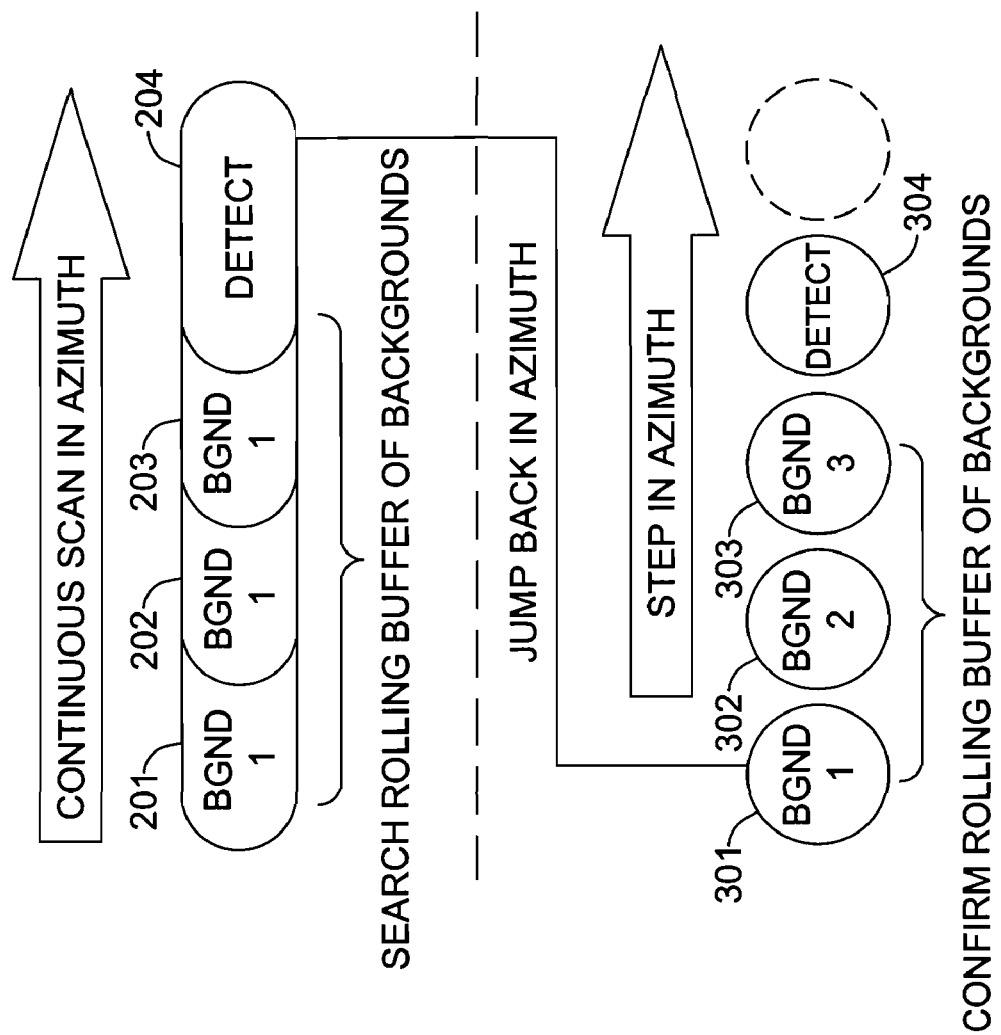
FIG. 13 is a diagram of a collection of backgrounds in the search and confirm modes.

The technical capabilities of BE may be noted. The removal of system artifacts and background features may be accomplished by using information from nearby spectra in the FOR. The nearby spectra may include the n, where as an example n=3, most recent background field of view (FOV) spectra as a scanner scans across the FOR. The recent spectra may be saved in a rolling buffer and used as a background for use at each new target FOV spectrum. The same approach may be used in a search mode and confirm mode with some tailoring for speed (search) versus accuracy (confirm). In the event of search mode detection, the command and control may direct the system to confirm mode. The azimuth and elevation angles of the FOV may be recorded, and the scanner be directed to jump back n azimuth angles to allow a collection of sufficient previous backgrounds in the confirm mode. The system may acquire n spectra and save it in the confirm mode rolling buffer. This approach is shown in FIG. 13, discussed herein, which is a diagram of a collection of backgrounds in the search and confirm modes.

For each field of view, a simplified model of the sensed radiance ($Spec_{sensed}$) may have three components which include the background radiance ($Spec_{back}$), the chemical cloud ($Spec_{cloud}$) if any, and the system self radiance ($Spec_{sys}$), which is often referred as the system artifacts, that is, if a chemical cloud is present, the $$Spec_{sensed}(fov_i) = Spec_{back}(fov_i) + Spec_{cloud}(fov_i) + Spec_{sys},$$

if a chemical cloud is not present, then $$Spec_{sensed}(fov_i) = Spec_{back}(fov_i) + Spec_{sys}.$$

One background removal technique may subtract the input spectrum, $Spec_{sensed}(fov_{in})$ from the spectrum of an adjacent FOV, $Spec_{sensed}(fov_1)$. Assuming the case that the input spectrum has a chemical cloud and the adjacent FOV does not have an agent cloud, then the difference spectrum may consist of the chemical cloud radiance and the radiance residue between the two FOV's. That is, $$Spec_{diff}(fov_{in}) = Spec_{sensed}(fov_{in}) - Spec_{sensed}(fov_1) = Spec_{cloud}(fov_{in}) + Spec_{back}(fov_{in}) - Spec_{back}(fov_1).$$

The system artifacts, which remain constant between the two FOV's, may be removed. If the backgrounds of the two FOV's are similar, the radiance residue may also be close to zero. In such case, the most prominent signature may be that of the chemical cloud. In the case when the two FOV backgrounds are different, this technique will not necessarily work well since the background residue may mask the agent signature.

The present BE approach may overcome changes in the background by adjusting the recent FOV spectrum to produce an "estimated background". The background estimation approach may compute its n estimated backgrounds based on the spectra from n previous FOV's as $$Spec_{estBack}(fov_{in}) = C_1 * Spec_{back}(fov_i) + C_2 + C_3 * X.$$

The estimated background may optimize the spectrum from a previous FOV to best fit the input spectrum in spectral regions outside of where the peaks of the target chemical lie. $C_2$ may remove offset differences and/or drift between the input spectrum and the previous FOV spectrum. $C_3$ may remove slope differences. $C_1$ may adjust for differences in the overall amplitude of background features. $C_1$, $C_2$ and $C_3$ may be computed for each background estimate. As a result, the chemical cloud signature may become prominent even in the presence of rapidly changing background FOV's, for instance, from low angle sky to high angle sky.

Several safety factors and signal enhancement may be incorporated in a BE algorithm. Limits may be set to $C_1$, $C_2$ and $C_3$ to prevent unreasonable adjustments. The n backgrounds may be treated independently. Any unreasonable estimate may be discarded and the remaining ones may be used. A boost factor may amplify the difference spectrum when the original input spectra are smooth, thus improving the agent signature for recognition under ideal-background conditions.

Since the BE approach may remove the system artifacts and remove background clutter peaks across the spectrum, the result is an improvement in small signal detection. The sensor-to-sensor performance variations caused by system artifacts may be reduced. Another advantage of the BE methodology may include more symmetric emission versus absorption performance by classifying an inverted difference spectrum and by removing artifacts and background/atmosphere clutter.

Figure 4:
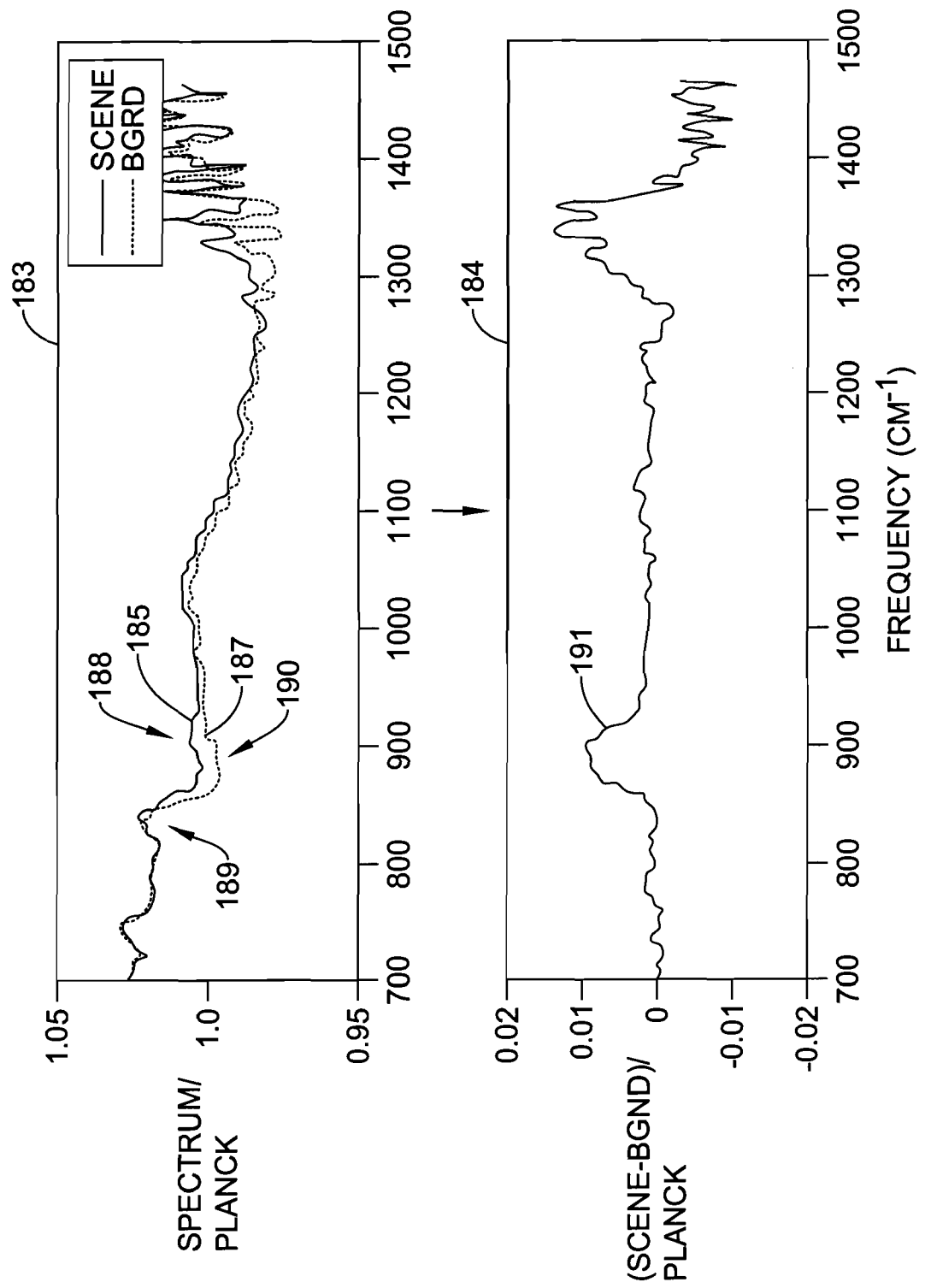
FIG. 4 shows graphs revealing a removal of system artifacts when going from the top graph to the bottom graph.

FIG. 4 shows graphs revealing a removal of system artifacts when going from the top graph 183 to the bottom graph 184. Modeling and simulation of a nitric acid (NA) cloud, which is the target chemical in this example, generated a scene spectrum, solid line 185 at horizon from the background spectra at dotted or shaded line 187. An NA peak may be indicated by arrow 188. Arrow 189 indicates a system artifact and arrow 190 indicates peaks and valleys. Improvement in extraction of the small NA signal may be observed in curve 191 at bottom graph 184 after the BE algorithm is applied to the data in the top graph 183.

Figure 5:
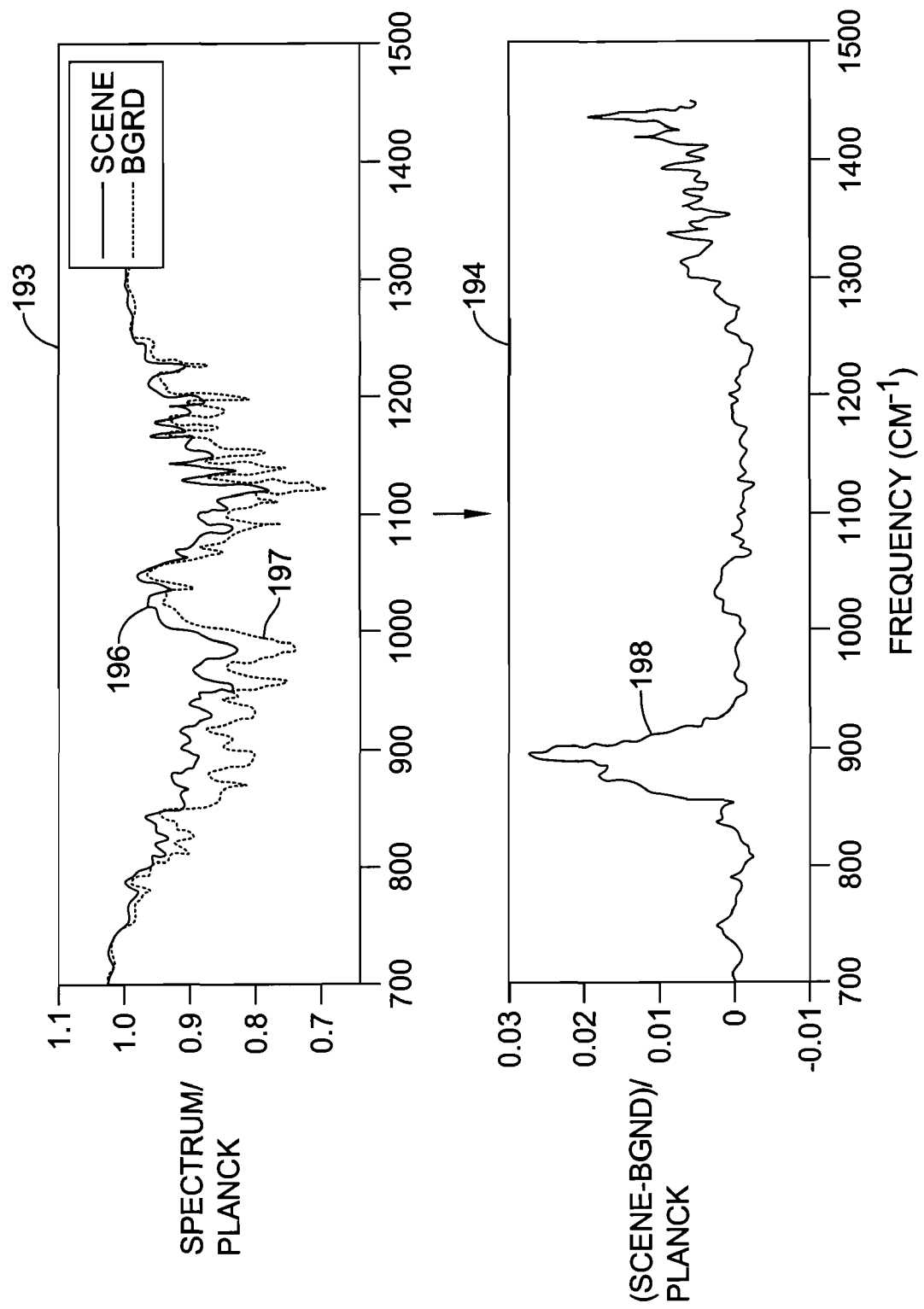
FIG. 5 shows graphs revealing nulling parameters during significant changes between target and background.

FIG. 5 shows upper graph 193 and lower graph 194 revealing effects of nulling parameters during significant changes between target and background. The scene is indicated by a solid line 196 and the background by dotted or shaded line 197. The graphs depict data simulation of a NA cloud at low sky when the spectrum changes significantly between target scene and background. Removal of the background 197 from scene 196 in top graph 193 may result in an identifiable target spectrum 198 in bottom graph 194.

The background estimation may be considered as part of preprocessing in the system. Thus, it may be applied to inputs of the system detection process regardless which chemical compound is intended to be detected. Differing chemical compounds may require selecting different spectral regions, where no specific chemical signature appears, to compute $C_1$, $C_2$, and $C_3$. The chemical-specific regions may be parameterized and stored as part of a coefficient file along with other chemical-specific parameters for feature extraction and classification. In summary, advantages of the BE approach may include an elimination of system artifacts, reduction in background clutter, and production of more consistent performance results across virtually all systems.

One may use the following process and equations to calculate the values for the parameters $C_1$, $C_2$ and $C_3$ in the equation for the estimated background (BE) spectrum, $$Spec_{estBgrd} = C_1 * Spec_{nearby} + C_2 + C_3 * X.$$

The calculation may use the current spectrum, $Spec_{current}$, and a recent nearby spectrum, $Spec_{nearby}$, each of length N. The process may be in the form of a Matlab™ script.

% N is the length of each spectrum (e.g., N=200 points)

$N$=length(Spec_current);

% MIdx is an array that defines the subset of points in the spectrum that are used
% to estimate the background. MIdx contains array indices into the spectrum.
% MIdx may exclude regions of the spectrum that are known a priori to be limited
% usefulness (e.g. due to instrument performance or atmospheric blocking). To % demonstrate this concept, this script excludes the first 10 and last 10 points in
% each spectrum.
% MIdx may also exclude the region(s) where the target peaks will be. To demonstrate
% this concept, this script excludes points 50 thru 80.
% The notation is, for any array X, the symbol X(MIdx) is the portion of array
% X picked out by MIdx.

$MIdx=[11:49, 81:190];$

% Create an array X that is a linear ramp with mean=0 and norm=1 when evaluated
% on the points in MIdx $X=[1:N]';$ $X=X-\text{mean}(X(MIdx));$ $X=X/\text{norm}(X(MIdx));$ % Create an array S2 that equals the reference background with % the slope and mean removed when evaluated on the points in MIdx.
% Note that s and t are scalars, and * is a vector dot product operator $s=\text{mean}(Spec\_nearby(MIdx));$ $t=X(MIdx)'*Spec\_nearby(MIdx);$ $S2=Spec\_nearby-s-X*t;$ % Calculate C1 by projecting S2 onto Spec_current
% Then ensure that C1 is within its reasonable upper and lower bounds $C1=S2(MIdx)'*Spec\_current(MIdx)\cdot/(S2(MIdx)'*S2(MIdx));$ $C1=\min(C1,C1upperBound);$ $C1=\max(C1,C1lowerBound);$ % Calculate specTmp, which is Spec_current with the contribution
% from C1*Spec_nearby removed.
% Then calculate the mean and slope parameters from specTmp
% evaluated on points in MIdx $specTmp=Spec\_current-(C1*Spec\_nearby);$ $C2=\text{mean}(specTmp(MIdx));$ $C3=X(MIdx)'*specTmp(MIdx);$ % vector dot product.

$Spec\_estBgnd=C1*Spec\_nearby+C2+X*C3;$

Figure 6:
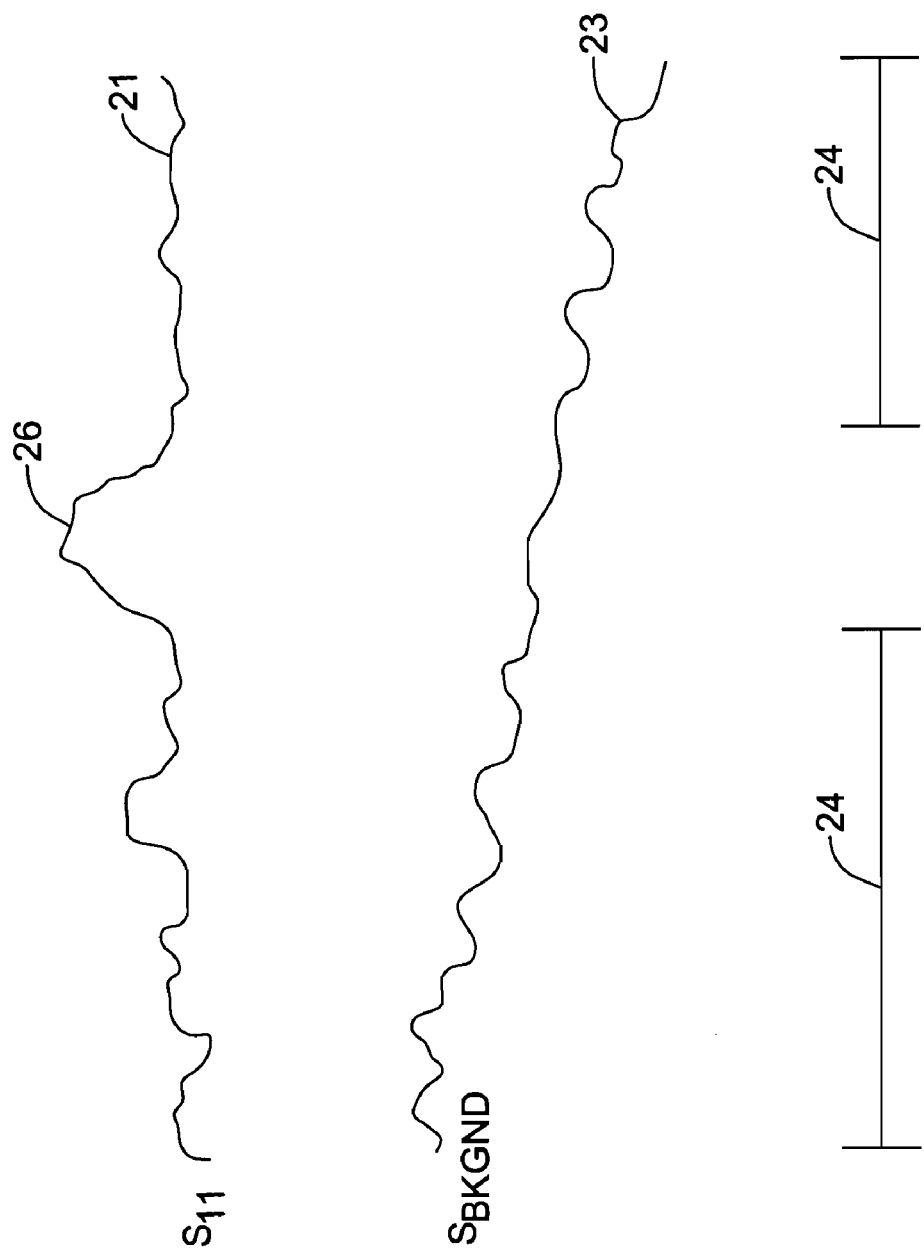
FIG. 6 is a diagram of a detected spectrum and background spectra with a tilt which may be compensated.

% Calculate the mean square difference evaluated on the points in MIdx $Spec\_diff=Spec\_current-Spec\_estBgnd;$ $MSD=\text{sqrt}(\text{sum}(Spec\_diff(MIdx)\cdot\hat{}2)/\text{length}(MIdx));$ FIG. 6 also shows the regions 24 and 25, outside of peak 26, of the background to zero out with the use of constants $C_1$, $C_2$ and $C_3$.

Figure 7:
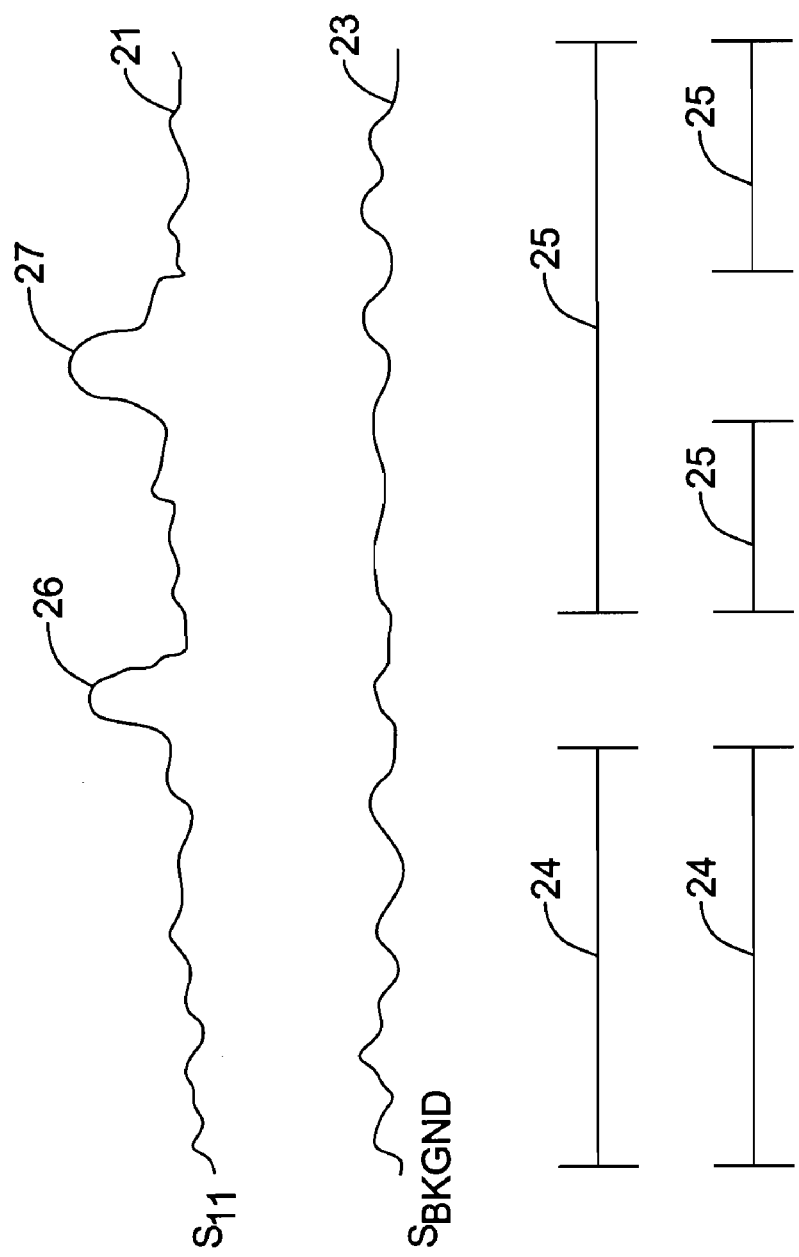
FIG. 7 is a diagram of a detected spectrum having two apparent peaks and background.

Spectrum $S_{11}$, curve 21, may have two or more peaks 26 and 27 as shown in FIG. 7. Because of an extra peak i.e., peak 27, a part of one of the regions, i.e., region 25, may be removed. These regions may be zeroed out.

Figure 8:
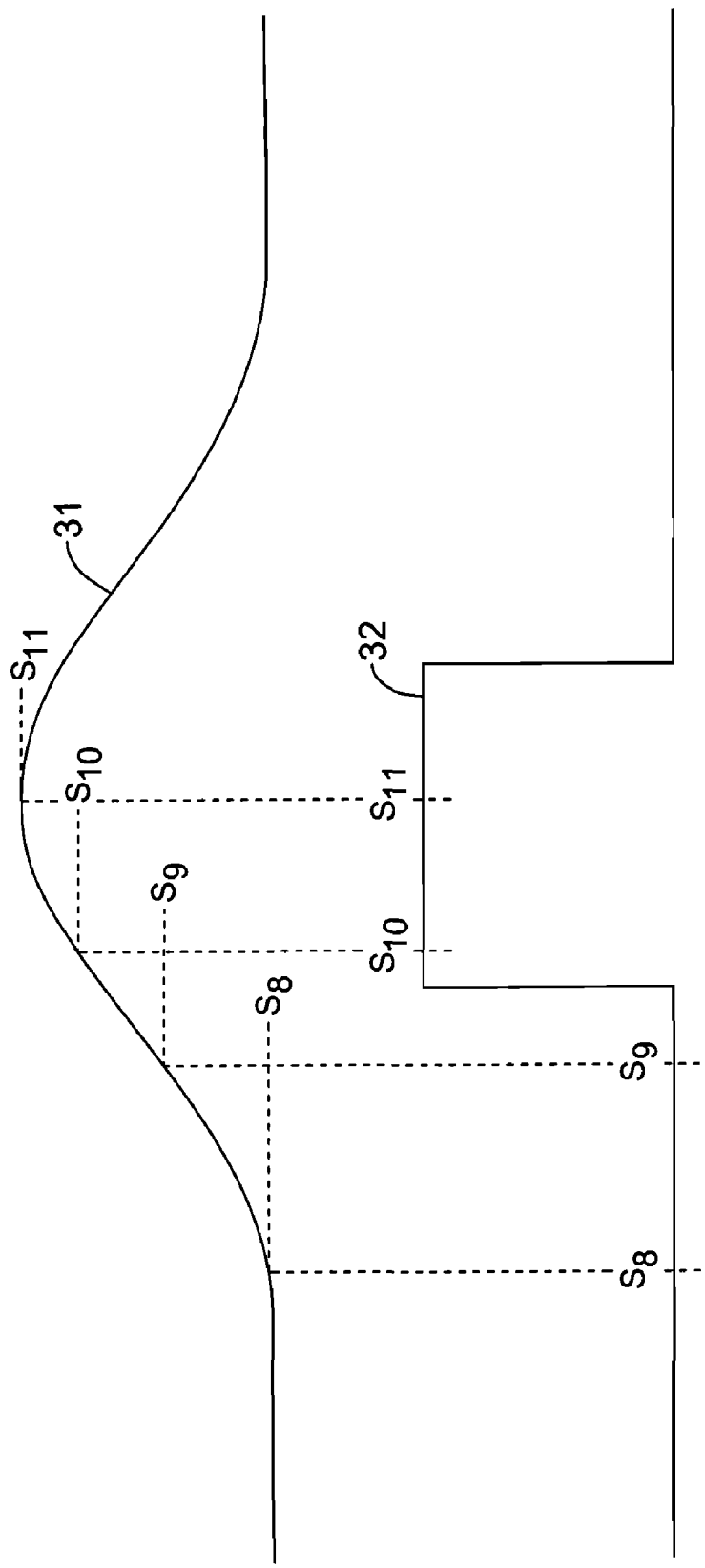
FIG. 8 is a diagram showing variations of spectra having background and chemical cloud and variation of the two combined.

As far as determining what a background should be, several backgrounds may be tried individually, such as $S_8$, $S_9$ and $S_{10}$ for current FOV $S_{11}$ in FIG. 8. $S_8$ and $S_9$ may change rapidly over time. $S_{10}$ may be regarded as changing less rapidly because it is more recent and thus is likely to be more like $S_{11}$.

The present system may be situated on a moving vehicle. The estimated background may constantly be changing because of the system's movement with the vehicle.

Figure 9:
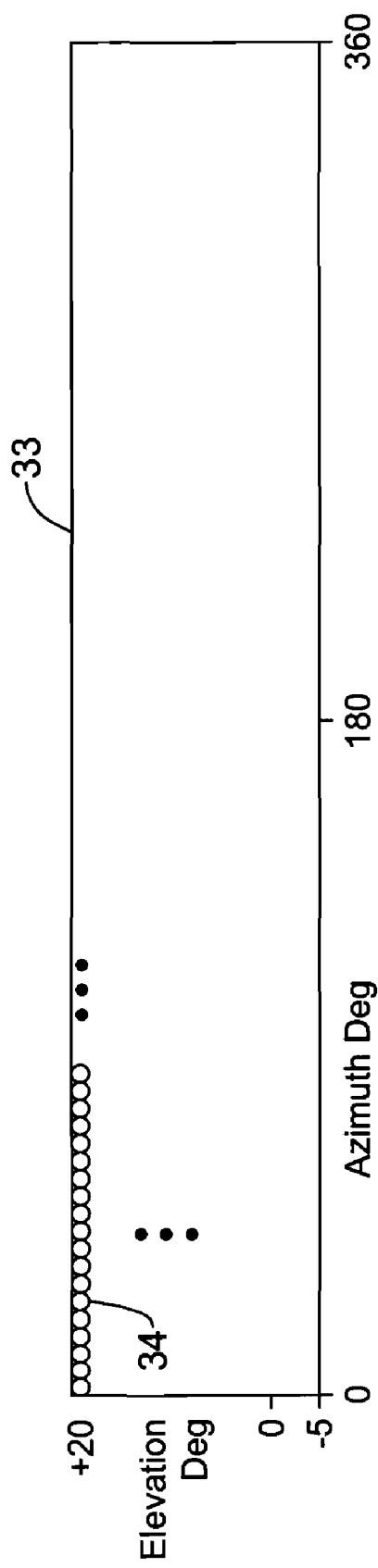
FIG. 9 is a diagram of a field of regard containing a series of FOV's.

Whether the system is on a moving vehicle or not, it may have a way of looking around for various clouds of, for example, a chemical agent. One way may include scanning about an azimuth and elevation as shown with fields of views (FOV's) converging a field of regard (FOR). FIG. 9 shows a field of regard 33 with a series of FOV's 34 shown as circles. FOV's may cover the whole FOR. One design of the scanning may be the FOV's as 1.5 degree diameter sized adjacent circles where the scan is like from one circle to another in an azimuth of 360 degrees to a plus twenty degrees. The system may scan from the lower portion of FOR 33 and move one row on up upon each rotation of the scan through 360 degrees of azimuth. Upon completion of a scan of FOR 33, the scan may be redone. There may be other patterns of scanning. A scanning apparatus may have selectors for various scanning patterns.

Figure 10:
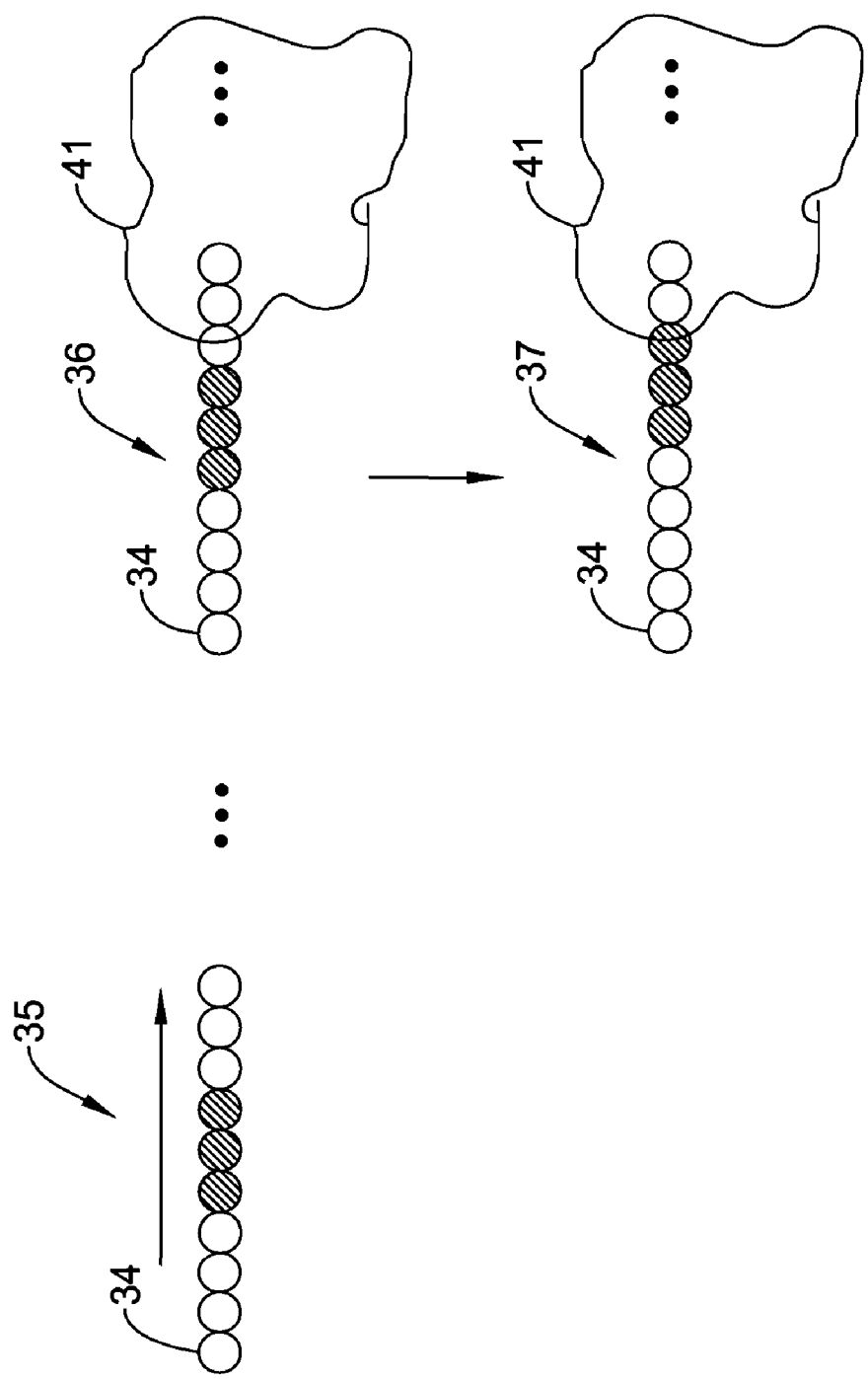
FIG. 10 is a diagram showing instances of increments of scanning a number of FOV's where a chemical cloud may exist or not.

Instances of increments of scanning are shown in FIG. 10. A number of FOV's 34 may be scanned. The shaded FOV's of group 35 may indicate background spectrums $S_8$, $S_9$ and $S_{10}$. The next FOV may represent spectrum $S_{11}$. These FOV's may continue on to a group 36 where the shaded FOV's indicate background spectrums $S_{27}$, $S_{28}$ and $S_{29}$. The next FOV may represent spectrum $S_{30}$. In group 36, spectrum 30 is shown to be partially entering a cloud 41. However, spectrum 36 may not reveal the target chemical of the cloud. In group 37, spectrum 30 is shown further in cloud 41 and thus improving appearance of the chemical agent of the cloud in spectrum 30. Spectra 28-29 may be regarded as background and used in calculating the $Spec_{DiFF}$.

Figure 11:
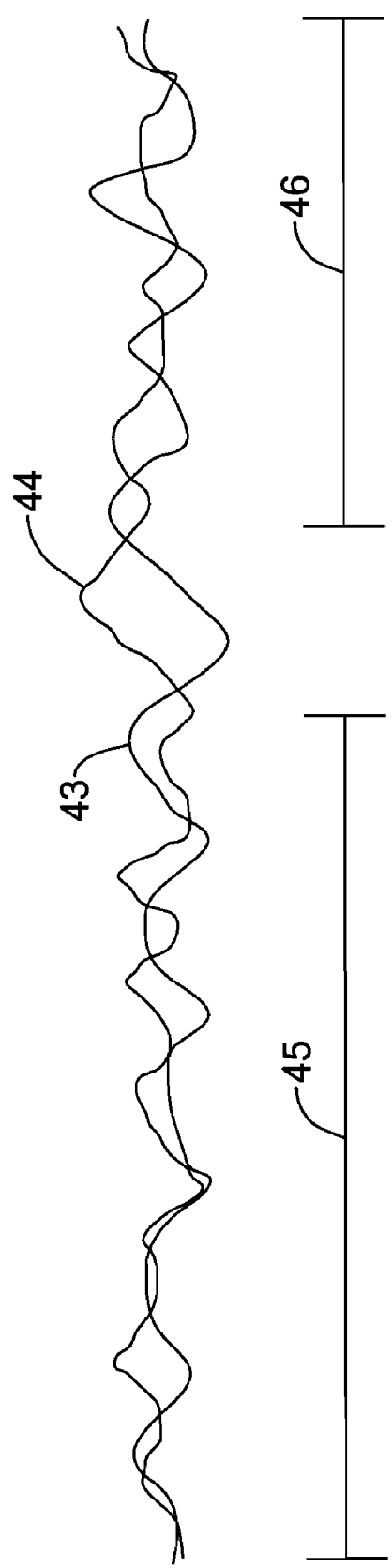
FIG. 11 is a diagram of several spectra having a residual so large as to not result in a useful spectral difference.

Reasonable results are a goal of the present system. First, one degree of reasonableness may include upper and lower bounds for C1, C2 and C3, as they relate to equation, $Spec_{Diff}=S_{11or30}-(Bgnd*C_1+C_2+C_3*X).$ Second, another degree of reasonableness may involve spectra 43 and 44 vastly different as shown in FIG. 11. The area of interest may be set out with regions 45 and 46 to be zeroed out with constants. However, the residual appears too large and this $Spec_{Diff}$ is not useful. For instance, a switch from a scene like a building to a scene like a sky may result in such a difference that one cannot pretend to use them. $S_8$-$S_{11}$ cannot necessarily use the $Spec_{Diff}$ equation because of possibly excessive residual.

Figure 12A:
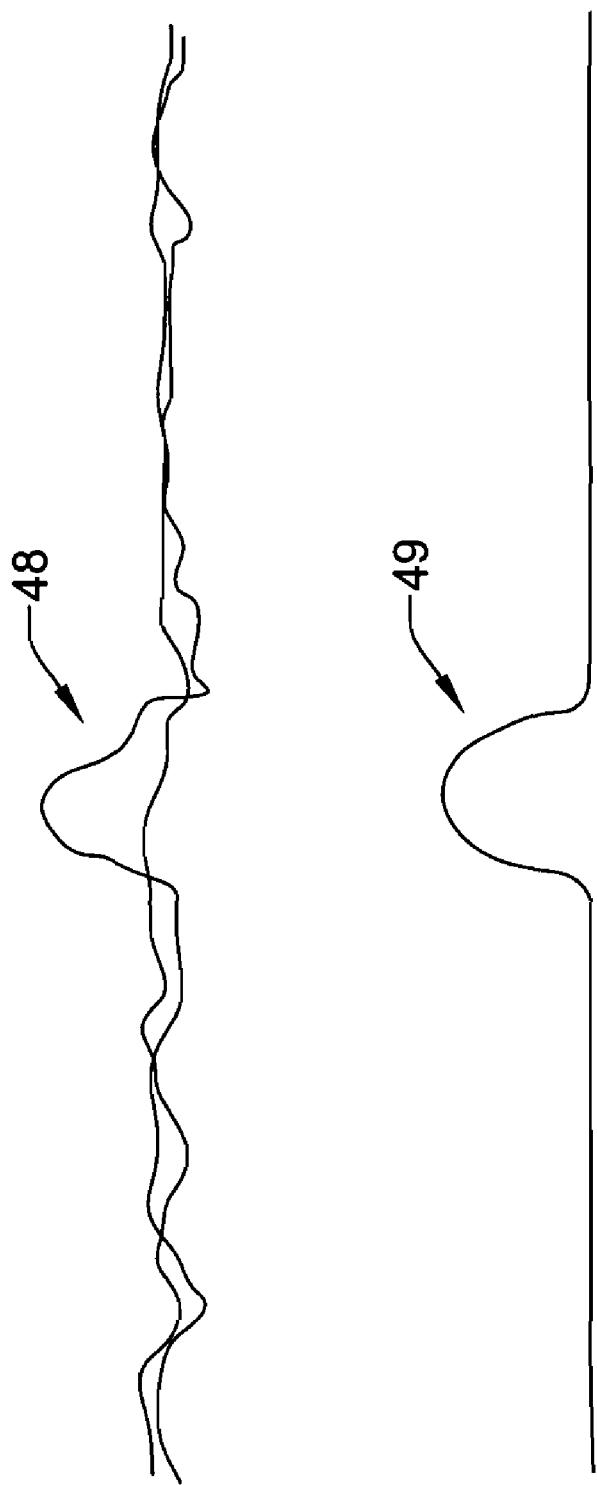
FIG. 12a is a diagram showing where there are small to negligible background peaks such that the signal after background removal (also shown) may be boosted or the threshold may be lowered for detection.
Figure 12B:
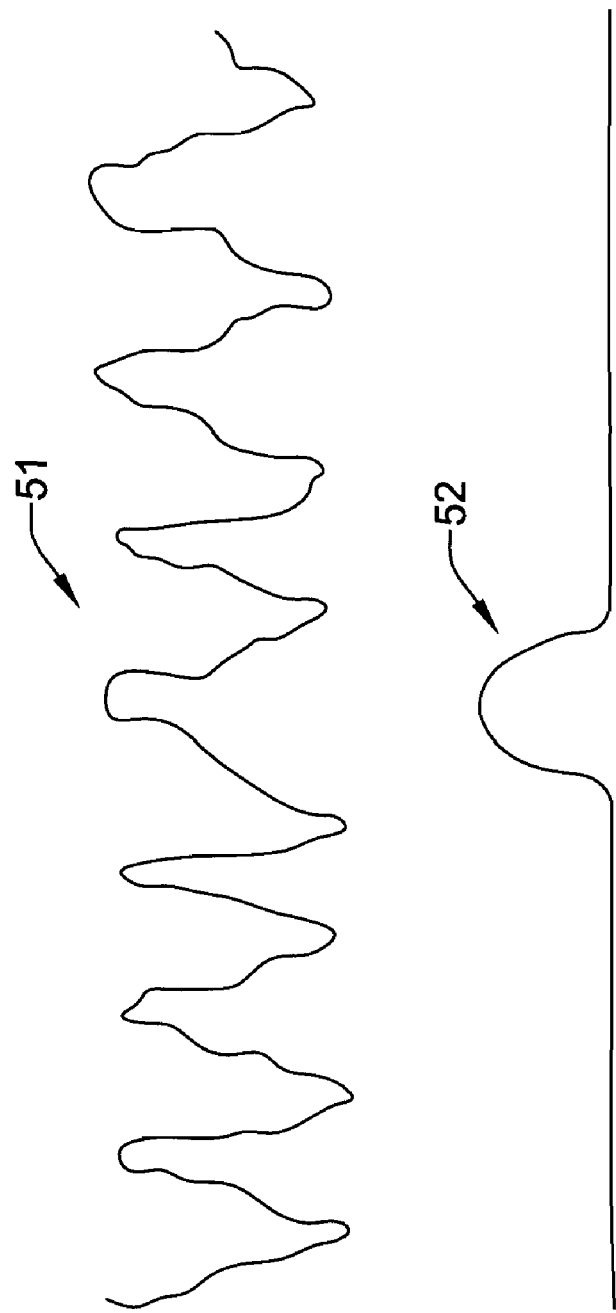
FIG. 12b is a diagram of spectra with large background peaks such that the signal after background removal (also shown) may be de-boosted or the threshold may be increased for detection.

Third, there may be two scenes with large spikes as in a diagram of FIG. 12b. Such two spectra substantially get significant residuals. There may be one spike just slightly larger than the other. One may boost or attenuate the $Spec_{Diff}$ for small or large peaks, respectively, in the original Bgnd and spectra. The spectra of FIG. 12a may be trusted more than the spectra of FIG. 11.

The sky may present large peaks in the spectra background. The subject could have residual peaks where two sets of peaks are subtracted but by some odds of chance happenings, the residual peaks could happen. It may be noted that terrain and buildings may provide relatively flat specs. A peak from a flat spec may be given more significance than one with peaks.

FIG. 12a is a diagram showing where there are small to negligible background peaks such that the signal after background removal (also shown) may be boosted or the threshold may be lowered for detection. FIG. 12b is a diagram of spectra with large background peaks such that the signal after background removal (also shown) may be de-boosted or the threshold may be increased for detection.

One may look at original two spectra. Subtracting two items with large peaks may result in large residuals. The difference should be higher than the higher threshold. The difference spectra may look the same. A signal to noise ratio is desired to be at least about 3 to 1. If there is, for instance, just five percent more signal than background, then the signal may be boosted. An example of the signal is shown as waveform 48 in FIG. 12a. A resultant $\text{Spec}_{Diff}$ may be like waveform 49. The signal may be boosted or the threshold may be attenuated or lowered for detection. In other words, the bar or requirement may be raised for detection. There may be a result having large bumps which can provide a noise immunity problem. A signal may result but it may not be a true signal. FIG. 12b shows an example of large bumps and the signal after background removal. The threshold may be adjusted, or the threshold may be fixed and the signal expanded or decreased. A multiple scale factor may be used to improve the signal.

Reasonableness may involve upper and lower bounds for the C constants, although the constants may be calculated. For example of bounds, $C_1$ should not be negative so that one does not flip results. An example range may be $0.5 < C_1 < 2.0$.

FIG. 13 reveals aspects of the scanner operation in terms of field of views (FOV's 34) for the region of regard (FOR 33) as discussed in FIGS. 1, 9 and 10. Backgrounds 201, 202 and 203 may be, for instance, specs $S_8$, $S_9$ and $S_{10}$, respectively, noted in a continuous scan in azimuth along with the present detect spec $S_{11}$, indicated as detect 204. The background specs 201, 202 and 203 may be stored on a rolling basis, e.g., the three previous specs, which may be specs, other than $S_8$, $S_9$ and $S_{10}$, in a search rolling buffer of backgrounds. This continuous approach may be regarded as a search mode for the background estimation algorithm. There may be a continuous scan azimuthally while acquiring and processing spectra. There may be a subtraction of the background (e.g., one or more of $S_8$, $S_9$, $S_{10}$) from the current spectrum ($S_{11}$) before feature extraction and classification are performed. Also an inversion may be tried which involves background minus the current spectrum. Both versions of subtraction may be applied for each individual background. One may switch from the search mode to the confirm mode upon a detection of the target chemical in the medium-resolution, search mode.

The confirm mode of the background estimation algorithm may proceed upon jumping back azimuthally from a point where the search detected. Three spectra may than be acquired at the first azimuth angle to initialize a confirm rolling buffer of backgrounds 301, 302 and 303, such as, for example, $S_8$, $S_9$ and $S_{10}$, respectively. One or more of the backgrounds 301, 302 and 303 may be a background for spec $S_{11}$, as indicated by a detect 304. One may step through the angle where the search was detected. At each azimuth step, the spectra may be processed like that of the search mode. A second time may be tried at each azimuth angle. It may be noted that multiple positives constitute detection.

Figure 14:
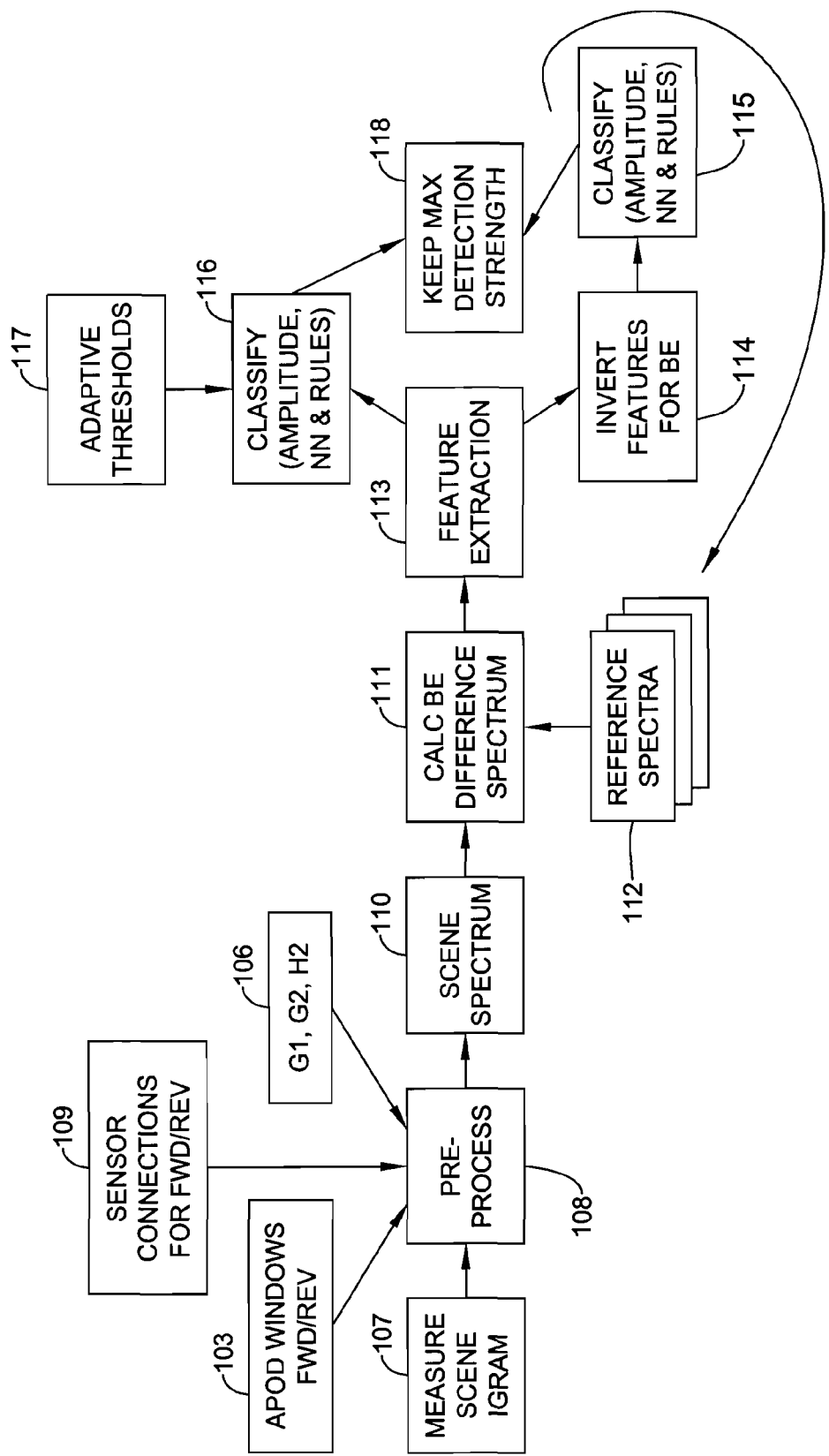
FIG. 14 is a flow diagram of an approach where the background estimation calculation may be done continuously during a spectra search mode.

FIG. 14 is a flow diagram of an approach where the background estimation calculation may be done continuously during a spectra search mode.

In the present specification, some of the matter may be of a hypothetical or prophetic nature although stated in another manner or tense.

Although the invention has been described with respect to at least one illustrative example, many variations and modifications will become apparent to those skilled in the art upon reading the present specification. It is therefore the intention that the appended claims be interpreted as broadly as possible in view of the prior art to include all such variations and modifications.

What is claimed is:

1. A method for spectral signal detection comprising:
scanning fields of view (FOV's) of a panoramic field of regard with a scanner;
capturing radiance in the FOV's with a spectrometer;
selecting a FOV having the spectrum of interest with a processor;
recalling a FOV's previous to the FOV having the spectrum of interest with the processor;
obtaining n estimated background spectra from the n FOV's, respectively, with the processor; and
determining a difference spectrum from each of the n estimated background spectra and the FOV having the spectrum of interest with the processor.

2. The method of claim 1, wherein:
$\text{Spec}_{EstBgnd\ FOV(si)} = C_1 * \text{Spec}_{FOV(i)} + C_2 + C_3 * X$;
$\text{Spec}_{EstBgnd}$ is an estimated background spectrum;
FOV(si) is the FOV having the spectrum of interest;
$\text{Spec}_{FOV(i)}$ is a background spectrum of an $i^{th}$ FOV;
X is a linear line for effectively adjusting a slope of the background spectrum of the $i^{th}$ FOV;
the $i^{th}$ FOV is one of the n FOV's;
$C_1$ is for adjusting differences in overall amplitude of background features;
$C_2$ is for removing offset and/or drift; and
$C_3$ is for removing slope differences.

3. The method of claim 2, wherein:
$\text{Spec}_{Diff} = \text{Spec}_{FOV(si)} - (C_1 * \text{Spec}_{FOV(i)} + C_2 + C_3 * X)$;
$\text{Spec}_{Diff}$ is a difference spectrum; and
$\text{Spec}_{FOV(si)}$ is the FOV having the spectrum of interest.

4. The method of claim 1, further comprising subtracting each of the n estimated background spectra of the n FOV's, from the spectrum of interest of the FOV having the spectrum of interest, with the processor.

5. The method of claim 4, further comprising subtracting the spectrum of interest of the FOV having the spectrum of interest, from each of the n estimated background spectra of the n FOV's, with the processor.

6. The method of claim 5, wherein:
the subtracting the spectrum of interest of the FOV having the spectrum of interest, from each of the n estimated background spectra of the n FOV's, and the subtracting each of the n estimated background spectra of the n FOV's from the spectrum of interest of the FOV having the spectrum of interest, result in 2n difference spectra;
one or more of the 2n difference spectra are subjected to a boosting factor by the processor; and
the boosting factor is dependent on an amount of background and/or atmospheric clutter in the spectrum of interest and/or the spectra of one or more of the n FOV's.

7. The method of claim 6, wherein the boosting factor represents confidence in one or more peaks of a boosted difference spectrum.

8. The method of claim 6, wherein:
if the spectrum of interest of the FOV having the spectrum of interest and/or the spectra of one or more of the n FOV's are relatively free of clutter, then the difference spectra may be amplified by the processor accordingly; and/or
if the spectrum of interest and/or the spectra of one or more of the n FOV's have strong clutter, then the difference spectra may be amplified less or attenuated by the processor.

9. The method of claim 7, each boosted difference spectrum is classified by the processor as having or not having a target chemical.

10. The method of claim 2, wherein constraints are applied to values of $C_1$, $C_2$ and/or $C_3$ by the processor to avoid over-correction.

11. The method of claim 2, wherein the constants $C_1$, $C_2$ and/or $C_3$ are automatically computed by the processor to maximally match background spectrum of the FOV having the spectrum of interest.

12. The method of claim 4, wherein:
  if a total energy of a difference spectrum exceeds a set threshold, then an estimated background spectrum used to obtain the difference spectrum is excluded from use for removal of a background spectrum from the FOV having the spectrum of interest; and
  if the difference spectrum is excluded, then the remaining n−1 estimated background spectra may be used by the processor for removal of the background spectrum from the FOV having the spectrum of interest.

13. A system for spectral signal detection comprising:
  a scanner;
  a spectrometer connected to the scanner; and
  a processor connected to the spectrometer; and
  wherein:
    the scanner is for directing fields of view (FOV's) of radiance;
    the spectrometer is for detecting and converting radiance in the FOV's into electrical signals; and
    the processor is for:
      processing the FOV's of spectra from the electrical signals;
      selecting an FOV having a spectrum of interest;
      recalling n FOV's previous to the FOV having the spectrum of interest;
      calculating n estimated background spectra from the n FOV's, respectively; and/or
      determining a difference spectrum from each of the n estimated background spectra and the FOV having the spectrum of interest.

14. The system of claim 13, wherein:
  $\text{Spec}_{EstBgnd\ FOV(si)} = C_1 * \text{Spec}_{FOV(i)} + C_3 * X$;
  $\text{Spec}_{EstBgnd}$ is an estimated background spectrum;
  FOV(si) is the FOV having the spectrum of interest;
  $\text{Spec}_{FOV(i)}$ is a background spectrum of an $i^{th}$ FOV;
  X is a linear line for effectively adjusting a slope of the background spectrum of the $i^{th}$ FOV;
  the $i^{th}$ FOV is one of the n FOV's;
  $\text{Spec}_{Diff} = \text{Spec}_{FOV(si)} - (C_1 * \text{Spec}_{FOV(i)} + C_2 + C_3 * X)$;
  $\text{Spec}_{Diff}$ is a difference spectrum;
  $\text{Spec}_{FOV(si)}$ is the FOV having the spectrum of interest;
  $C_1$ is for adjusting differences in overall amplitude of background features;
  $C_2$ is for removing offset and/or drift; and
  $C_3$ is for removing slope differences.

15. The system of claim 13, wherein the processor is further for:
  subtracting each of the n estimated background spectra of the n FOV's, from the spectrum of interest of the FOV having the spectrum of interest; and
  subtracting the spectrum of interest of the FOV having the spectrum of interest, from each of the n estimated background spectra of the n FOV's.

16. The system of claim 15, wherein:
  the subtracting the spectrum of interest of the FOV having the spectrum of interest, from each of the n estimated background spectra of the n FOV's, and the subtracting each of the n estimated background spectra of the n FOV's from the spectrum of interest of the FOV having the spectrum of interest, result in 2n difference spectra;
  one or more of the 2n difference spectra are subjected to a boosting factor; and
  the boosting factor is dependent on an amount of background and/or atmospheric clutter in the spectrum of interest and/or the spectra of one or more of the n FOV's.

17. The system of claim 14, wherein:
  constraints are applied to values of $C_1$, $C_2$ and/or $C_3$ to avoid over-correction; and
  wherein the constants $C_1$, $C_2$ and/or $C_3$ are automatically computed by a processor to maximally match background spectrum of the FOV having the spectrum of interest.

18. The system of claim 15, wherein:
  if a total energy of a difference spectrum exceeds a set threshold, then an estimated background spectrum used to obtain the difference spectrum is excluded from use for removal of a background spectrum from the FOV having the spectrum of interest; and
  if the difference spectrum is excluded, then another one of the remaining n−1 estimated background spectra may be used for removal of the background spectrum from the FOV having the spectrum of interest.

19. A method for removing background spectra from a FOV having a spectrum of interest, comprising:
  scanning adjacent FOV's from a field of regard with a scanner;
  capturing radiance in the adjacent FOV's from the field of regard with a spectrometer;
  selecting a FOV having the spectrum of interest with a processor;
  recalling n FOV's previous to the FOV having the spectrum of interest with the processor;
  calculating n estimated background spectra for the FOV having the spectrum of interest, based on the n FOV's, respectively, with the processor; and
  determining n difference spectra from the n estimated background spectra and the FOV having the spectrum of interest with the processor.

20. The method of claim 19, further comprising selecting the best difference spectrum of the n difference spectra with the processor.

* * * * *